(12) United States Patent
Bennett et al.

(10) Patent No.: US 7,367,951 B2
(45) Date of Patent: May 6, 2008

(54) SYSTEM AND METHOD FOR DETECTING CARDIOVASCULAR HEALTH CONDITIONS USING HEMODYNAMIC PRESSURE WAVEFORMS

(75) Inventors: Tommy D. Bennett, Shoreview, MN (US); Mark Choi, Minneapolis, MN (US); David A. Igel, Lino Lakes, MN (US); Michael R. S. Hill, Minneapolis, MN (US); Teresa A. Whitman, Dayton, MN (US); Douglas A. Hettrick, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 398 days.

(21) Appl. No.: 11/044,617

(22) Filed: Jan. 27, 2005

(65) Prior Publication Data

US 2006/0167359 A1 Jul. 27, 2006

(51) Int. Cl.
*A61B 5/02* (2006.01)

(52) U.S. Cl. .................. 600/485; 600/500; 600/508

(58) Field of Classification Search ......... 600/485–507
See application file for complete search history.

(56) References Cited

U.S. PATENT DOCUMENTS

| 5,265,011 A * | 11/1993 | O'Rourke | 600/485 |
| 6,171,252 B1 * | 1/2001 | Roberts | 600/485 |
| 6,887,207 B2 * | 5/2005 | Hettrick | 600/485 |
| 2001/0016690 A1 * | 8/2001 | Chio | 600/485 |
| 2004/0210145 A1 * | 10/2004 | Satoh et al. | 600/500 |
| 2006/0116590 A1 * | 6/2006 | Fayram et al. | 600/508 |

* cited by examiner

*Primary Examiner*—Robert L. Nasser, Jr.
*Assistant Examiner*—Karen E Toth
(74) *Attorney, Agent, or Firm*—Paul H. McDowall; Steve Bauer (57) ABSTRACT

A cardiovascular analysis system and method includes an implantable medical device with a sensor positioned to sense a hemodynamic pressure over time. The implantable medical device generates hemodynamic pressure waveform data based upon the hemodynamic pressure sensed. A processor analyzes the hemodynamic waveform data to provide an indication of cardiovascular health based upon prominent peaks in the hemodynamic waveform data.

14 Claims, 6 Drawing Sheets

SYSTEM AND METHOD FOR DETECTING CARDIOVASCULAR HEALTH CONDITIONS USING HEMODYNAMIC PRESSURE WAVEFORMS

BACKGROUND OF THE INVENTION

The present invention relates to a system and method for detecting adverse health conditions based upon analysis of hemodynamic waveforms derived from pressures in a heart.

It is possible to obtain cardiovascular data, for healthcare and research purposes, using an implantable medical device (IMD) such as an implantable hemodynamic monitor (IHM), together with a pressure sensor lead that senses blood pressure within a heart chamber and an electrogram (EGM) of the heart. The IHM senses absolute blood pressure values, and the patient is also provided with an externally worn atmospheric pressure reference monitor record contemporaneous atmospheric pressure values.

A cardiovascular analysis system using the IHM can be programmed to sense and calculate various hemodynamic parameters.

The IHM is programmed and interrogated employing an external programmer or a PC to accumulate trend data at a programmable resolution.

The IHM and the atmospheric pressure reference monitor can transmit by telemetry the sensed and stored pressure and other data to a nearby interactive remote monitor for temporary storage of the data. The interactive remote monitor periodically transmits accumulated data to a remote data processing center that can process the data to develop trend data that the attending physician can review, along with other patient data derived in patient examinations and interviews, to assess cardiovascular health.

Such an IHM system implanted in patients suffering from adverse cardiovascular health conditions can accumulate date-stamped and time-stamped blood pressure data that can be of use in determining the condition of the heart and or vascular system over an extended period of time and while the patient is clinically tested or is engaged in daily activities. Various other IHM functions and uses of EGM, pressure and other parameter data accumulated in an IHM are disclosed in U.S. Pat. Nos. 5,368,040, 5,417,717, 5,564,434, 6,104,949, 6,155,267, 6,280,409, 6,275,707, 6,309,350, and 6,438,408, and U.S. Pat. App. Ser. Nos. 2003/0199779 and 2004/0167410.

Adverse health conditions may include coronary artery disease (CAD) and pulmonary hypertension (PHT) (commonly referred to as PAH). CAD occurs when coronary arteries, which supply blood to heart muscle, become hardened and narrowed due to atherosclerosis, which is a buildup of plaque on inner walls or a lining of arteries. Blood flow to the heart is reduced as plaque hardens and narrows the coronary arteries. This decreases the oxygen supply to the heart muscle, which can lead to numerous heart conditions and heart failure.

PHT occurs when blood pressure in a pulmonary artery rises above normal levels. PHT is associated with an increased resistance to blood flow in blood vessels, which can cause a heart to work harder to try to push blood through those vessels. PHT can be categorized as primary or secondary. Secondary PHT is when a pre-existing disease causes PHT, while primary PHT is when the cause of PHT is unknown and therefore PHT is considered the primary disease.

It is desirable to use an IHM system to monitor cardiovascular condition in order for healthcare providers to provide diagnose illness and to monitor adverse health conditions. Thus, a system and method for detecting health conditions using hemodynamic pressure waveform data is needed.

BRIEF SUMMARY OF THE INVENTION

The present invention relates to a cardiovascular analysis system that includes an implantable medical device with a sensor positioned to sense a hemodynamic pressure over time. The implantable medical device generates hemodynamic pressure waveform data based upon the hemodynamic pressure sensed. A processor analyzes the hemodynamic waveform data to provide an indication of cardiovascular and cardiopulmonary health based upon prominent peaks in the hemodynamic waveform data.

The invention further includes a method of cardiovascular analysis. The method includes sensing a hemodynamic pressure, generating a hemodynamic pressure waveform representing the hemodynamic pressure sensed for a cardiovascular pulse cycle, and providing an indication of whether an adverse cardiovascular condition is present based upon a shape of the hemodynamic waveform over a systolic time interval.

DETAILED DESCRIPTION

Figure 1:
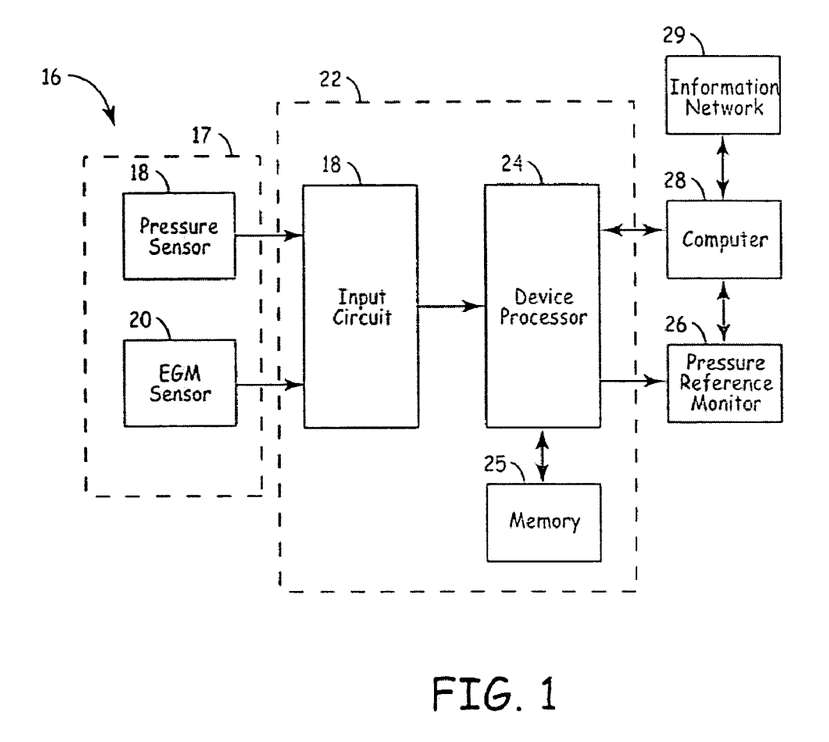
FIG. 1 is a block diagram of a cardiovascular analysis system.

FIG. 1 is a block diagram of cardiovascular analysis system 16, which senses hemodynamic pressures in a patient's heart and analyzes sensed hemodynamic pressure data to assess health conditions of the patient. System 16 includes sensor lead 17 (carrying hermetically sealed pressure sensor 18 and electrogram (EGM) sense electrode 20), implantable hemodynamic monitor (IHM) 22 (including input circuit 23, device processor 24 and memory 25, atmospheric pressure reference monitor (PRM) 26, computer 28, and information network 29.

In one embodiment, the IHM 22 is a CHRONICLE® Model 9520 IHM, described in commonly assigned U.S. Pat. No. 5,368,040. In other embodiments, hemodynamic data can be sensed and recorded by an IMD that also functions as a pacemaker, cardioverter, defibrillator, and/or drug pump. The sensor lead 17 can be a Medtronic® Model 4328A, and the PRM 26 can be a Medtronic® Model 2955HF, both available from Medtronic, Inc., Minneapolis, Minn. Computer 28 can be a Medtronic® Model 9790 programmer or a PC with CHRONICLE® software.

Hemodynamic data can include indicators of mechanical heart function, for example, hemodynamic pressures at various cardiovascular locations, such as in the right ventricle, left ventricle, right atrium, left atrium, pulmonary arteries, and systemic arteries. Input circuit 23 is a signal processing circuit that receives a pressure signal representative of blood pressures in the heart (e.g., in the right ventricle) from pressure sensor 18 and an electrical signal representative of the electrical activity of the heart from EGM sensor 20. Input circuit 23 may sample, demodulate or otherwise process the signals received from pressure sensor 18 and EGM sensor 20.

Device processor 24 derives hemodynamic pressure waveform data and hemodynamic parameters from the processed pressure and electrical signals received from input circuit 23. The hemodynamic waveform data and hemodynamic parameters are stored in memory 25 on a beat-by-beat basis, minute-to-minute basis, hour-to-hour basis, or on some other basis.

Because IHM 22 senses absolute blood pressure values, the patient is also provided with externally worn PRM 26. Contemporaneous atmospheric pressure values produced by PRM 26 are communicated to computer 28 along with data from IHM 22.

Computer 28 accumulates trend data that is stored in a memory at a programmable resolution. System 16 can be connected to information network 29, which includes an Internet-accessible database of cardiovascular information obtained using system 16. Information network 29 can be used to provide patient information to computers and medical personnel located remotely from the patient.

Hemodynamic waveform data and hemodynamic parameters are analyzed with system 16 to assess health conditions of the patient based upon shapes of the hemodynamic waveform data. This analysis can be performed by various components of system 16, such as IHM 22, computer 28, and a processing node on information network 29. Waveform shape can be identified through comparisons to categories of waveform shapes, which are established based upon relationships to health conditions, for detecting and monitoring adverse health conditions with system 16.

Figure 2:
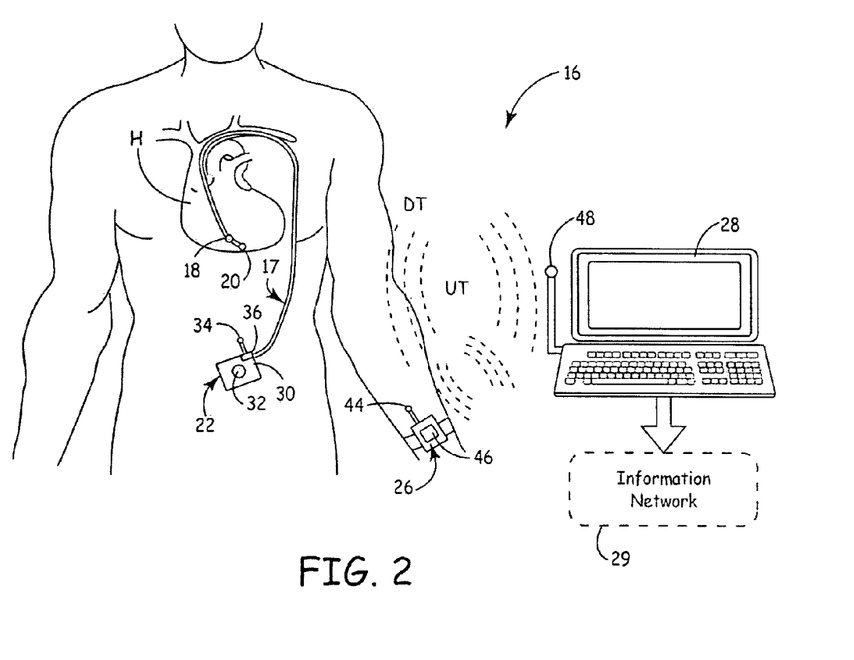
FIG. 2 is an illustration of the cardiovascular analysis system of FIG. 1.

FIG. 2 illustrates a cardiovascular analysis system 16 used to obtain and analyze hemodynamic data sensed within a heart. System 16 includes IHM 22, sensor lead 17, PRM 26, and computer 28. IHM 22 includes hermetically sealed housing 30, activity sensor 32, transmitter/receiver 34, and lead connector header 36. PRM 26 includes transmitter/receiver 44, and can optionally include timepiece function 46. Computer 28 is operatively connected to receiver/transmitter 48.

In FIG. 2, uplink telemetry (UT) and downlink telemetry (DT) transmissions are shown between receiver/transmitter 48 and both transmitter/receiver 34 of IHM 22 and transmitter/receiver 44 of PRM 26.

Figure 3:
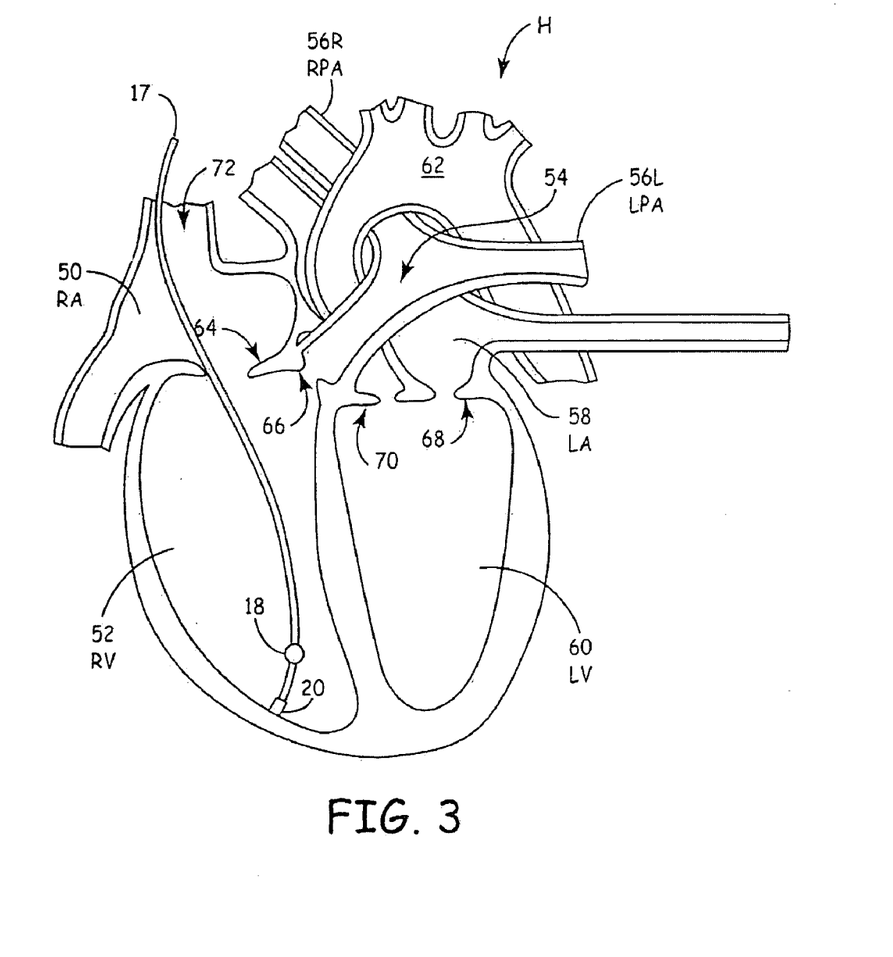
FIG. 3 is a detailed illustration of a hemodynamic pressure sensor positioned in a heart.

FIG. 3 is a detailed view of pressure sensor 18 positioned in heart H, which includes right atrium (RA) 50, right ventricle (RV) 52, pulmonary artery 54 including right pulmonary artery (RPA) 56R and left pulmonary artery (LPA) 56L, left atrium (LA) 58, left ventricle (LV) 60, aorta 62, right atrioventricular valve 64, pulmonary valve 66, left artioventricular valve 68, aortic valve 70, and superior vena cava 72. As shown in FIG. 3, pressure sensor 18 is positioned in right ventricle 52. Pressure sensor 18 could be positioned in other cardiovascular locations, such as in any other chamber of heart H, in pulmonary artery 54, or in the left or right pulmonary artery 56L or 56R.

Figure 4:
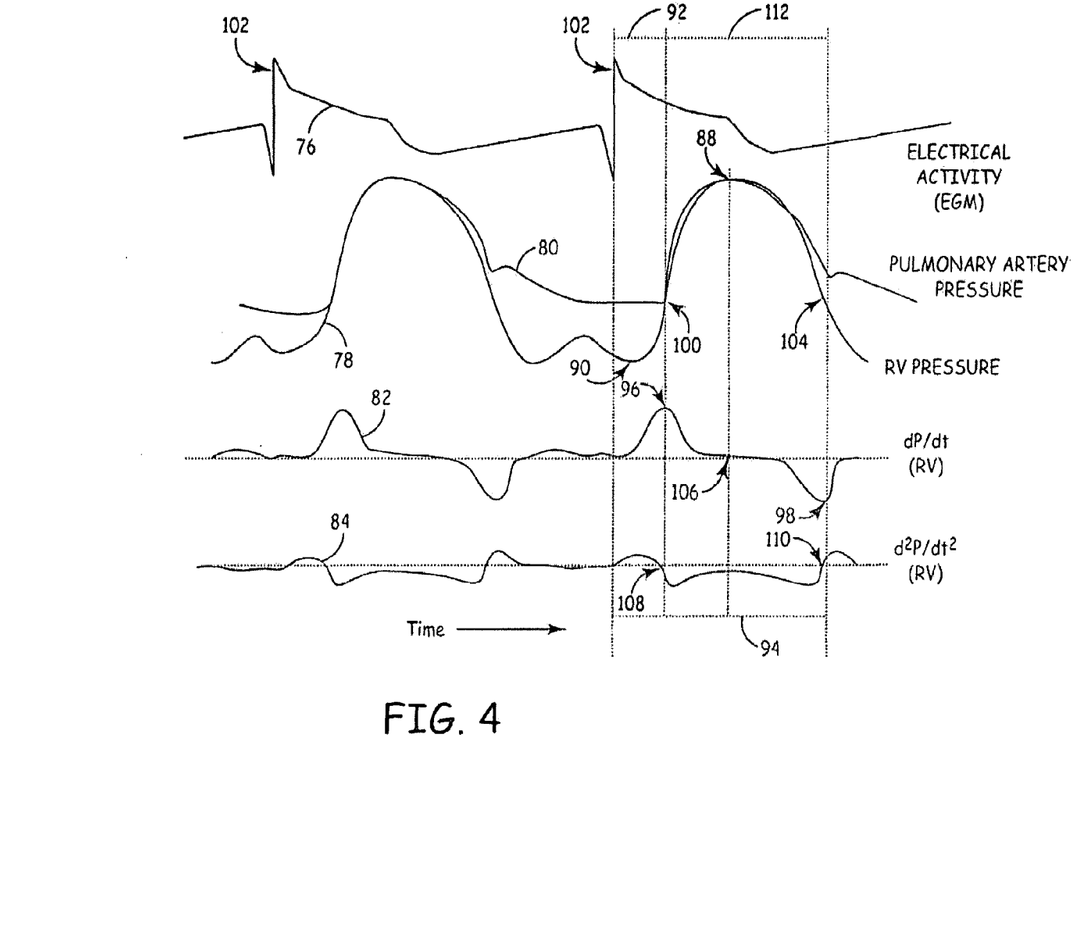
FIG. 4 is a diagram showing waveforms of cardiovascular data obtainable from the cardiovascular analysis system of FIG. 1.

System 16 can be used to obtain cardiovascular waveform data, which can be analyzed to assess health conditions of a patient. FIG. 4 is a diagram showing examples of waveforms of cardiovascular data obtainable from system 16. The waveforms relate, without limitation, to electrical activity (i.e., EGM) 76, right ventricle (RV) pressure 78, pulmonary artery pressure 80, the first derivative (dP/dt) of RV pressure 82, and the second derivative (d2P/dt2) of RV pressure 84. Hemodynamic parameters are sampled at a sampling rate of about 256 samples per second (256 Hertz), digitized and stored in memory registers. The data can be stored as waveforms by system 16.

IHM 22 is programmed to sense and calculate, for example, RV systolic pressure 88 (i.e., a maximum or peak pressure in a sampling window), RV diastolic pressure 90 (i.e., a first pressure sample in a sampling window), pulse pressure (where pulse pressure=RV systolic pressure−RV diastolic pressure), pre-ejection interval (PEI) 92, systolic time interval (STI) 94, peak positive change in pressure dP/dtmax 96 (synonymously called +dP/dtmax), peak negative change in pressure dP/dtmin 98 (synonymously called −dP/dtmax), estimated pulmonary artery diastolic pressure (ePAD) 100, R-waves 102, RR-lnterval (RRI) 103 (i.e., the heart beat interval), patient activity level, and heart rate (HR) (where HR=(60,000 milliseconds/minute)/(RRI in msec/beat)). Other waveform parameters can be obtained, such as inflection point 104 corresponding to the closing of the pulmonary valve, point 106 where dP/dt 82 first reaches a negative value, and points 108 and 110 where d2P/dt2 84 becomes negative and then becomes positive again. Pulse width 112, measured between dP/dtmax 96 and dP/dtmin 98, is also identified.

Additional cardiovascular information can be derived from the hemodynamic values identified above. For instance, times at which the pulmonary valve opens and closes during a cardiovascular pulse cycle can be estimated as times 96 and 98 when dP/dtmax and dP/dtmin occur, respectively. Additionally, even where a pressure sensor obtains RV hemodynamic data, information relating to LV hemodynamic conditions can generally be inferred from the RV data.

Figure 5:
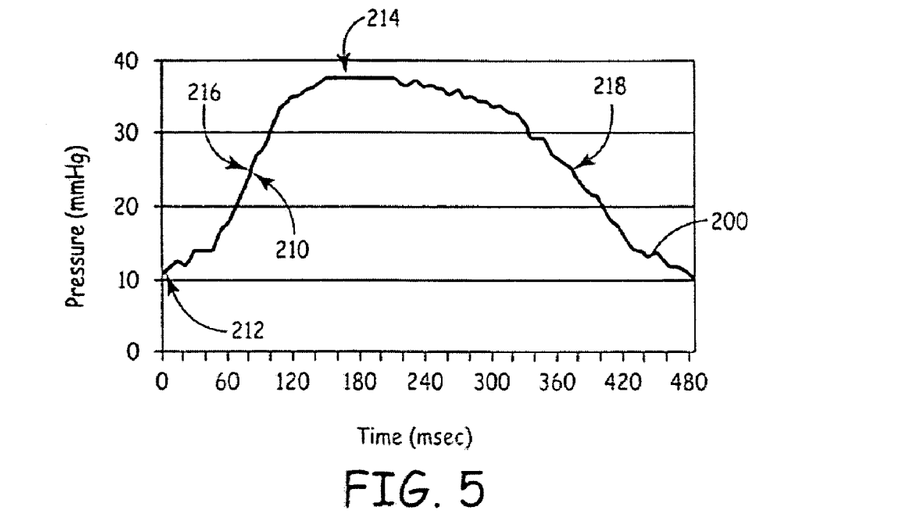
FIG. 5 is a representation of a hemodynamic pressure waveform having only a single prominent pressure rise.

FIG. 5 is a graph of a hemodynamic pressure waveform 200 for a cardiovascular pulse cycle. Cardiovascular data samples are generally taken in a sampling window corresponding to a cardiovascular pulse cycle. That sampling window is a time interval for hemodynamic sensing of approximately 500 milliseconds (ms) that begins following electrical activation of the heart. IHM 22 is programmed so that sampling windows occur every four days during times when a patient's activity levels are low (e.g., when sleeping). Sampling windows can occur at any other desired periodicity. In addition, periods of increased sampling resolution can be activated, such as while an acute event relating to cardiovascular health is occurring.

Analysis of hemodynamic waveform data and hemodynamic parameters with system 16 can assist in assessing adverse cardiovascular health conditions, including health conditions that affect heart function. Coronary artery disease (CAD) is a common adverse cardiovascular health condition that can lead to heart failure and death. Pulmonary hypertension (PHT) (commonly referred to as PAH) is another adverse cardiovascular health condition that affects vessel compliance and dispensability, and can lead to heart failure and death. Other health conditions, such as diabetes, can also have an effect on cardiovascular functions.

CAD generally occurs when coronary arteries, which supply blood to heart muscle, become hardened and narrowed. CAD, regardless of a location of a blocked coronary artery, can increase pulmonary arterial impedance and elevate pulmonary arterial pressure by initially affecting pulmonary venous pressure.

Diabetes can affect cardiovascular functions. Persons with diabetes mellitus can become hypervolemic due to increased serum glucose levels after meals. Increased blood volume due to elevated osmotic pressure can stiffen pulmonary vasculature and increase overall arterial impedance.

PHT generally occurs when blood pressure in a pulmonary artery rises above normal levels. According the World Health Organization, normal pressure ranges when at rest are 15-30 mmHg for Psys, 6-12 mmHg for Pdias, and 9-18 mmHg for mean pulmonary artery pressure (Pmean). It is clinically accepted that a patient having Pmean greater than 25 mmHg at rest has PHT. A patient is considered to have severe PHT if his or her Pmean exceeds 40 mmHg. Pmean can be estimated from hemodynamic parameters obtainable with system 16 using the following equation:

$$P_{mean(arterial)} = \frac{1}{3}P_{sys(RV)} + \frac{2}{3}ePAD$$

Alternatively, using time intervals obtainable using system 16, Pmean can be estimated according to the following equation, such as that described in U.S. patent application Ser. No. 09/997,753, entitled "Method and Apparatus for Measurement of Mean Pulmonary Artery Pressure From a Ventricle in an Ambulatory Monitor":

$$P_{mean(arterial)} = P_{sys(RV)} \times \frac{STI}{RRI} + ePAD \times \frac{RRI - STI}{RRI}$$

PHT may be a complication of other adverse health conditions such as CAD and diabetes mellitus.

System 16 permits detection of adverse health conditions, which affect risks of death. More particularly, adverse cardiovascular conditions such as PHT and CAD, as well as other adverse health conditions such as diabetes and syncope, can be detected using an analysis of hemodynamic pressure waveforms generated from hemodynamic pressures sensed within a chamber of the heart.

It is possible to distinguish categories of hemodynamic pressure waveforms based upon shapes of those waveforms. Two such categories are hemodynamic pressure waveforms having a single prominent primary peak (PPP) and those having both a prominent principal peak and a prominent secondary peak (PSP) that corresponds to systolic pressure. Adverse health conditions can be detected based upon categorization of hemodynamic pressure waveform shapes.

PPP waveforms constitute a first category of hemodynamic pressure waveforms. PPP waveforms have a substantially smooth, single initial rise in hemodynamic pressure from Pdias to Psys values. Psys corresponds to an overall peak value of a PPP waveform. In PPP waveforms, pressure generally decreases from Psys for a remainder of a cardiovascular pulse cycle, though pressure can decrease at varying rates (i.e., a relatively small secondary "peak" can appear in the waveform as pressure decreases from Psys).

FIG. 5 is a representation of a hemodynamic pressure waveform 200 having only a single prominent pressure rise 210. Pressure values of the hemodynamic pressure waveform 200 increase through a single prominent rise (e.g., through single prominent pressure rise 210) from first sample 212, corresponding to Pdias, to peak value 214, corresponding to Psys. Between points corresponding to opening 216 and closing 218 of pulmonary valve 66, there is only the single prominent pressure rise 210 in waveform 200 to peak systolic value 214.

PSP waveforms are another category of hemodynamic pressure waveforms. PSP waveforms include both a prominent primary pressure rise and a prominent secondary pressure rise between Pdias and Psys values. In PSP waveforms, the prominent primary pressure rise is synonymously called a "shoulder" of the prominent secondary pressure rise, because the prominent secondary pressure rise corresponds to an overall peak pressure value for a cardiovascular pulse cycle (Psys).

Figure 6:
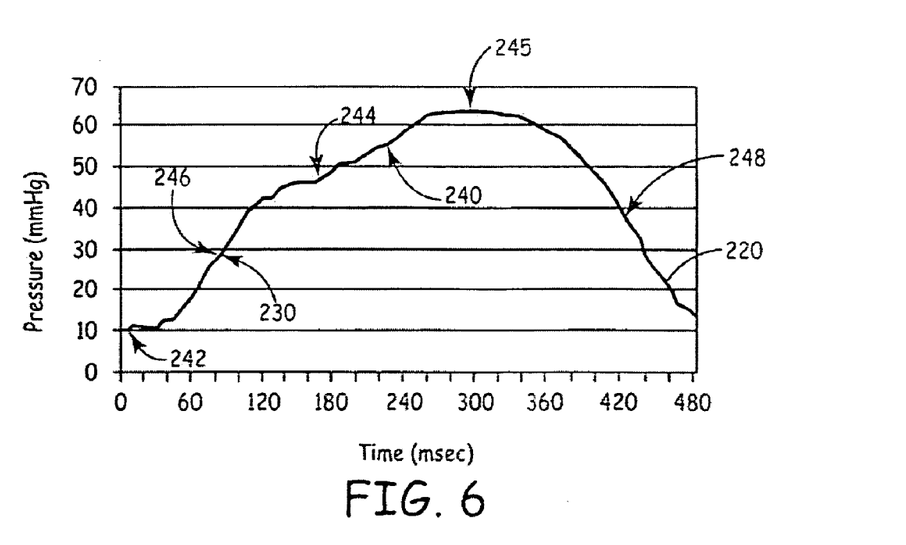
FIG. 6 is a representation of a hemodynamic pressure waveform having a prominent primary pressure rise and a prominent secondary pressure rise.

FIG. 6 is a representation of a hemodynamic pressure waveform 220 having prominent primary pressure rise 230 and prominent secondary pressure rise 240 between first sample 242, corresponding to Pdias, and peak value 245, corresponding to Psys. Between points corresponding to opening 246 and closing 248 of pulmonary valve 66, there are two prominent pressure rises in waveform 220. Pressure values of waveform 220 increase from first sample 242, corresponding to Pdias, to relative peak value 244. From relative peak value 244, pressure values of waveform 220 then increase to overall peak value 245, corresponding to Psys. Prominent primary pressure rise 230 corresponds to an increase in pressure from first sample 242 to relative peak value 244, and prominent secondary pressure rise 240 corresponds to an increase in pressure from relative peak value 244 to overall peak value 245 (i.e., to Psys).

"Wave reflection" describes wave propagation in walls of the blood vessel that occurs after ventricular contraction begins as a wave encounters a stiffened and/or narrowed portion and backwards reflection occurs. In a healthy person, reflection wave velocity is not fast enough to affect RV systolic pressure, and wave reflection may actually be beneficial. However, as arteries stiffen and/or narrow, reflection wave speeds generally increase in the pulmonary arterial system, causing wave reflection to have an additive effect on RV pressures. That additive effect is related to adverse cardiovascular conditions, which can lead to heart failure and death. The magnitude of wave reflection, which relates to reflection wave speed, is enlarged by increased arterial impedance. In addition, an abrupt change in distensibility of arteries can cause a marked increase in wave reflection.

It is believed that PSP waveforms relate to wave reflection in patients with high pulmonary arterial impedance. In other words, wave reflection has an augmenting effect on pressures within the heart. PSP waveforms are seen in persons having adverse health conditions that increase arterial impedance, such as PHT, CAD and diabetes. Where wave reflection is of a significant magnitude, the backwards wave reflection is believed to relate to a prominent secondary rise in pressure associated with PSP waveforms. For example, as shown with hemodynamic pressure waveform 220 of FIG. 6, prominent secondary pressure rise 240 corresponds to peak pressure value 245 (i.e., Psys), which is larger than relative peak pressure value 244 corresponding to prominent primary pressure rise 230. Prominent primary pressure rise 230 is related to contraction of the heart. Prominent secondary pressure rise 240 is related to wave reflection of a magnitude significant enough to augment pressure within the heart.

Occurrences of prominent secondary pressure rises can be detected in a number of ways. First, hemodynamic pressure waveforms can be analyzed manually through visual inspection by appropriate personnel. Visual inspection involves categorizing hemodynamic pressure waveforms as PPP or PSP according to shapes of those waveforms as depicted on a display by system 16. Second, hemodynamic pressure waveforms can be analyzed through an automated process, which can supplement or supplant a visual inspection process. Automated processes can be conducted using commercially available analysis software or custom analysis software.

Hemodynamic pressure waveforms are categorized as PPP or PSP based on an analysis to determined if a PSP shape is present. There are numerous ways to categorize waveform shape, and the various methods of categorization can be used individually or in combination. First, hemodynamic pressure waveforms can be identified as PSP if they have (a) a peak pulse pressure value (i.e., Psys) that occurs after a first predetermined period of waveform capture, such as after about the first 210 milliseconds (msec) of waveform capture, and (b) a dP/dt value greater than a predetermined value during a second predetermined period of waveform capture, such as between about 188 msec and about 312 msec of waveform capture.

Second, PSP waveforms can be identified by looking at the pulse width time interval, measured between dP/dtmax and dP/dtmin, and determining if an overall peak value (corresponding to a Psys value) occurs more than halfway through that interval (i.e., the Psys value occurs closer in time to dP/dtmin than to dP/dtmax).

Third, an Augmentation Index (AI) can be used. AI is a measure of a difference in pressure between prominent primary and secondary peaks of a hemodynamic pressure waveform over Ppulse (AI=(Psecondarypeak−Pprimarypeak)/Ppulse). Locations (in time) of prominent peaks, for determining associated pressure values, can be identified by calculating dP/dt and d2P/dt2 for a hemodynamic pressure waveform and determining where dP/dt and d2P/dt2 have values equal to zero. PPP waveforms can be detected where the AI is generally negative, and PSP waveforms can be detected where the AI is generally positive.

Fourth, a Shoulder Index (SI) can be used. The SI is a measure of a difference in pressure between prominent primary and secondary peaks of a hemodynamic pressure waveform over the pressure at the primary peak (SI=(Psecondarypeak−Pprimarypeak)/Pprimarypeak). The SI is always a positive value. PPP waveforms can be detected where the SI is generally less than a predetermined value (e.g., SI<1.0), and PSP waveforms can be detected where the SI is generally greater than a predetermined value (e.g., SI>1.0).

It will be recognized that other methods of detecting PSP waveforms are possible, such as by template matching, and the foregoing methods and criteria are provided by way of example, and not limitation.

Once a PSP has been detected in one or more hemodynamic waveforms, a characterization can be made regarding a presence of an adverse health condition. Detection of a PSP generally corresponds to the presence of an adverse cardiovascular condition such as PHT, CAD, and/or other conditions that affect arterial impedance of the patient. Such a characterization of a person's health can be useful in diagnosing adverse health conditions, monitoring a known adverse cardiovascular health condition, devising a treatment program, and in monitoring a treatment program.

PHT can be treated with drugs that reduce Pmean. Patients with PHT caused by chronic thrombotic or embolic diseases are widely treated with anticoagulant drugs. Patients who develop PHT indirectly from conditions such as left atrial or left ventricular heart failure are commonly treated with drugs such as calcium channel blockers, nitric oxide, prostacyclin, endothelin antagonist, and sildenafil, which normally reduce pressures and resistance in a pulmonary vascular system. It is believed that a reduction in arterial impedance will reduce a load on the LV and therefore increase stoke output. However, even with treatment for increased arterial impedance, mortality rates for patients with PHT are relatively high. Most PHT patients die from heart failure or sudden cardiac death. This may be explained in that an expected increase in stroke volume due to reduced arterial pressure may be offset by a decrease in inotropic state, which consequently reduced stroke volume again. Thus, pure hemodynamic pressure data can be combined with flow data to improve calculation of more detailed and informative wave characteristics, such as calculation of a reflection coefficient and a backward wave arrival time via Fourier analysis. It is possible to derive flow data from hemodynamic pressure data. Thus, pure hemodynamic pressure data and flow data derived from it can be used together in diagnosis and treatment settings.

Analysis of hemodynamic pressure waveforms with system 16 can also be used to monitor a treatment program. A patient diagnosed with an adverse health condition, such as PHT or CAD, may undergo a treatment program. Effectiveness of a treatment program can be monitored using hemodynamic pressure waveform data to create a feedback loop. Healthcare providers can obtain feedback on patient health conditions from analysis of hemodynamic pressure waveforms, which can indicate changes in severity of an adverse health condition and can also indicate remission of the adverse health condition. Healthcare providers can adjust treatment accordingly, based upon the feedback loop. Patients can react with varying levels of sensitivity to drugs. Feedback from the feedback loop can be used, for example, to adjust dosages of drugs.

Figure 7:
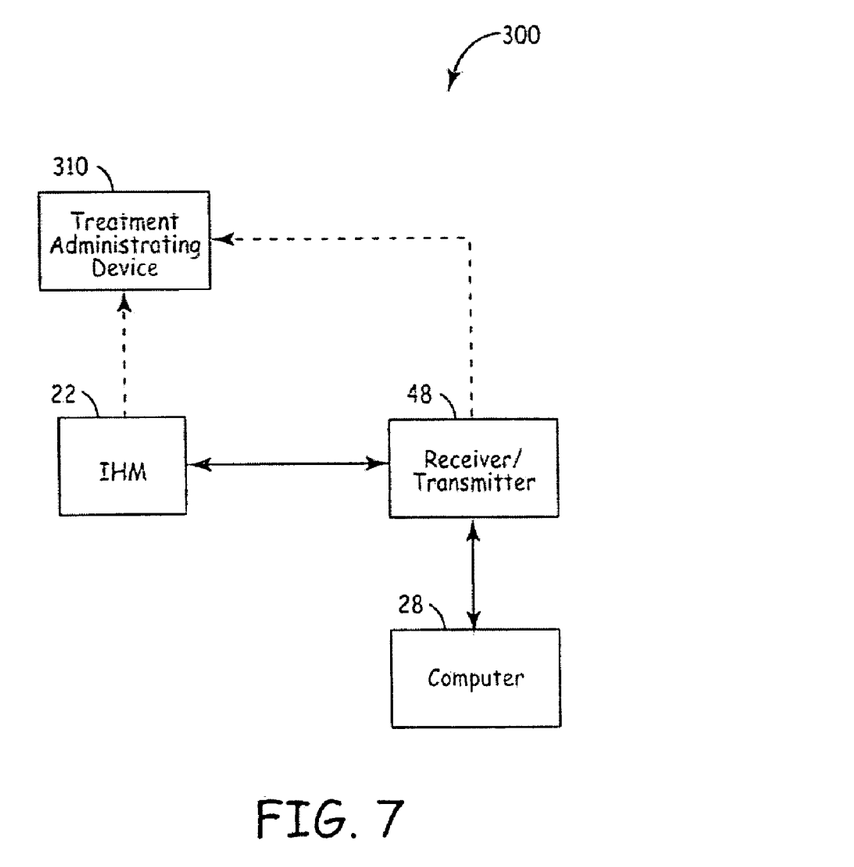
FIG. 7 is a block diagram of a treatment system.

In addition, analysis of hemodynamic pressure waveforms can be used in administering a treatment program. FIG. 7 is a block diagram of treatment system 300, which includes IHM 22, receiver/transmitter 48, computer 28, and treatment administering device 310. In one embodiment, treatment administering device 310 is an IMD, such as a drug pump, pacemaker, cardioverter, and/or defibrillator.

Feedback relating to health conditions obtained from analysis of hemodynamic waveforms obtained using IHM 22 can be used in conjunction with treatment administering device 310, which can correlate administration of a treatment to results of the analysis. Treatment administering device 310 can be responsive to commands issued directly from IHM 22 and/or from computer 28 (via receiver/transmitter 48). In a further embodiment, IHM 22 and treatment administering device 310 are combined as a single IMD.

Experimental data supports an association, discussed above, between hemodynamic pressure waveform shape and cardiovascular health. Most generally, certain hemodynamic parameters have a correlation with hemodynamic pressure waveform shape. For example, Psys, dP/dtmin, STI and Ppulse are significantly greater with PSP waveforms than with PPP waveforms.

EXAMPLES

The following examples relate to experiments conducted to observe whether patients having predominant PSP waveforms collected using the IHM system described above had any common health diagnoses upon implantation of the IHM 22. Table 1 summarizes a first example study showing a correlation between type of health condition and hemodynamic pressure waveform shape, where p-values less than 0.05 are statistically significant.

TABLE 1

| Health Condition | Diagnosis for Disease On Implantation | # of Patients | Patients with PPP Waveforms | Patients with PSP Waveforms | Percentage of Patients with PSP Waveforms | P-Value |
|---|---|---|---|---|---|---|
| PHT | Yes | 30 | 13 | 17 | 56.7% | <0.0001 |
|  | No | 67 | 55 | 12 | 17.9% |  |
| CAD | Yes | 52 | 29 | 23 | 44.2% | <0.0001 |
|  | No | 45 | 39 | 6 | 13.3% |  |

Data in Table 1 shows that PHT and CAD are health conditions with correlations to hemodynamic pressure waveform shape. PHT and CAD are correlated with PSP waveforms.

In looking at the correlation between PSP waveforms and PHT, a example study was conducted with 84 patients each having at least three months of hemodynamic pressure waveform data using the IHM system described above and having no detected instances of sensor failure. Of those patients, 18 had severe PHT (Pmean>40 mmHg), 56 had mild PHT (25 mmHg<Pmean<40 mmHg), and 10 had no PHT (Pmean<25 mmHg). A median pulmonary arterial pressure for the 84 patients was 31.2 mmHg. A difference of two ratios method was used to compare associations between hemodynamic pressure waveform shape and PHT. Table 2 summarizes comparisons of "at least mild PHT vs. no PHT", "severe PHT vs. non-severe PHT" and "greater than median PA pressure vs. less than median PA pressure", where a statistically significant association is found where Z>1.65.

TABLE 2

|  | PPP | PSP | Percentage of Patients with PSP Waveforms |
|---|---|---|---|
| At Least Mild PHT vs. No PHT |  |  |  |
| 74 patients with $P_{mean}$ > 25 mmHg | 48 | 26 | 35.1% |
| 10 patients with $P_{mean}$ < 25 | 9 | 1 | 10.0% |
|  |  |  | Z = 7.39 |
| Severe PHT vs. Non-Severe PHT |  |  |  |
| 18 patients with $P_{mean}$ > 40 mmHg | 2 | 16 | 88.9% |
| 66 patients with $P_{mean}$ < 40 mmHg | 55 | 11 | 16.7% |
|  |  |  | Z = 8.57 |
| Greater than Median PA Pressure vs. Less than Median PA Pressure |  |  |  |
| $P_{mean}$ > 31.2 mmHg | 21 | 21 | 50.0% |
| $P_{mean}$ < 31.2 mmHg | 36 | 6 | 14.3% |
|  |  |  | Z = 6.79 |

Table 2 further supports the correlation between PSP waveform shape and PHT.

Thus, it will be recognized that the present invention permits inferences as to health conditions of a patient, which can be detected, identified, and characterized based upon analysis of hemodynamic waveform data sensed within the heart. Such analysis can be used in healthcare and research settings for diagnostic, treatment, and monitoring purposes.

Although the present invention has been described with reference to preferred embodiments, workers skilled in the art will recognize that changes may be made in form and detail without departing from the spirit and scope of the invention. For instance, while reference is made to analysis of hemodynamic pressure waveforms, such analysis can be conducted using data that corresponds to hemodynamic pressure waveforms (such as impedance, cardiac accelerometry, etc.).

What is claimed is:

1. A cardiovascular analysis system comprising:
an implantable medical device having a sensor adapted to sense a hemodynamic pressure in a heart over time, wherein the implantable medical device generates hemodynamic pressure waveform data based upon the sensed hemodynamic pressure; and
a processor for analyzing the hemodynamic pressure waveform data to provide an indication of cardiovascular and cardiopulmonary health based upon prominent peaks in the hemodynamic pressure waveform data
wherein the processor indicates an adverse health condition that correlates to identification of a prominent primary peak and a prominent secondary peak of the hemodynamic pressure waveform data, and wherein the prominent secondary peak corresponds to a systolic pressure of a cardiovascular pulse cycle,
wherein the processor identifies a prominent secondary peak of the hemodynamic waveform data when a peak pressure value of the hemodynamic pressure waveform data occurs after about 210 milliseconds of hemodynamic pressure sensing and a first derivative of the hemodynamic pressure waveform data includes a value greater than about 128 mmHg/sec between a period of hemodynamic pressure sensing occurring between about 188 and about 312 milliseconds of sensing.

2. A cardiovascular analysis system comprising:
an implantable medical device having a sensor adapted to sense a hemodynamic pressure in a heart over time, wherein the implantable medical device generates hemodynamic pressure waveform data based upon the sensed hemodynamic pressure; and
a processor for analyzing the hemodynamic pressure waveform data to provide an indication of cardiovascular and cardiopulmonary health based upon prominent peaks in the hemodynamic pressure waveform data,
wherein the processor identifies a Shoulder Index for the hemodynamic pressure waveform data, and wherein an adverse cardiovascular condition corresponds to a Shoulder Index greater than about one.

3. A system according to claim 2, wherein the processor provides a signal related to an adverse cardiovascular health condition based at least in part upon certain prominent peaks in the hemodynamic pressure waveform data that correspond to the adverse health condition.

4. A system according to claim 3, wherein the adverse cardiovascular health condition comprises pulmonary hypertension.

5. A system according to claim 3, wherein the adverse cardiovascular health condition comprises coronary artery disease.

6. A system according to claim 2, wherein the processor identifies a prominent primary peak of the hemodynamic pressure waveform data, and wherein the prominent primary peak corresponds to a systolic pressure of a cardiovascular pulse cycle.

7. A system according to claim 2, wherein the processor identifies an Augmentation Index for the hemodynamic pressure waveform data, and wherein an adverse cardiovascular condition corresponds to a generally positive Augmentation Index.

8. A system according to claim 2, and further comprising means for providing a treatment based upon the indication of cardiovascular health.

9. A method of cardiovascular analysis, the method comprising:
   sensing a hemodynamic pressure in a heart;
   generating a hemodynamic pressure waveform representing the hemodynamic pressure sensed for a cardiovascular pulse cycle;
   providing an indication of whether an adverse cardiovascular condition is present based upon a shape of the hemodynamic waveform over a systolic time interval;
   identifying a prominent primary peak of the hemodynamic pressure waveform;
   identifying a prominent secondary peak of the hemodynamic pressure waveform, corresponds to the systolic pressure, and wherein identification of the prominent secondary peak correlates to indication of an adverse cardiovascular health condition,
   wherein a prominent secondary peak of the hemodynamic waveform is identified when a peak pressure value of the hemodynamic pressure waveform occurs after about 210 milliseconds of hemodynamic pressure sensing and a first derivative of the pressure waveform includes a value greater than about 128 mmHg/sec between a period of hemodynamic pressure sensing occurring between about 188 and about 312 milliseconds of sensing.

10. A method of cardiovascular analysis, the method comprising:
    sensing a hemodynamic pressure in a heart;
    generating a hemodynamic pressure waveform representing the hemodynamic pressure sensed for a cardiovascular pulse cycle; and
    providing an indication of whether an adverse cardiovascular condition is present based upon a shape of the hemodynamic waveform over a systolic time interval,
    wherein the processor identifies a Shoulder Index for the hemodynamic pressure wave form data, and wherein an adverse cardiovascular condition corresponds to a Shoulder Index that is greater than about 1.0.

11. A method according to claim 10, wherein the indication of the adverse cardiovascular condition indicates pulmonary hypertension.

12. A method according to claim 10, wherein the indication of the adverse cardiovascular condition indicates coronary artery disease.

13. A method according to claim 10, wherein the cardiovascular condition corresponds to a generally positive Augmentation Index.

14. A method according to claim 10, and further comprising transmitting the hemodynamic pressure waveform to a processing device for analysis.

* * * * *

UNITED STATES PATENT AND TRADEMARK OFFICE
CERTIFICATE OF CORRECTION

| | | |
|---|---|---|
| PATENT NO. | : 7,367,951 B2 | Page 1 of 1 |
| APPLICATION NO. | : 11/044617 | |
| DATED | : May 6, 2008 | |
| INVENTOR(S) | : Mark Choi et al. | |

It is certified that error appears in the above-identified patent and that said Letters Patent is hereby corrected as shown below:

Title page item [75] Inventor, delete "Douglas A. Hettrick, Andover, MN" and insert in place there of --Douglas A. Hettrick, Blaine, MN--.
Col. 11, line 29, delete "waveform, corresponds" and insert in place there of
--waveform, wherein the prominent secondary corresponds--

Signed and Sealed this

Thirtieth Day of December, 2008

JON W. DUDAS
*Director of the United States Patent and Trademark Office*